United States Patent [19]

Tarello et al.

[11] Patent Number: 4,713,061
[45] Date of Patent: Dec. 15, 1987

[54] CARTRIDGE WITH UNIVERSAL PLASTIC HUB

[75] Inventors: William R. Tarello, Bethesda; Linda A. Gordon, Germantown, both of Md.; T. Daniel Whalen, Trenton, N.J.

[73] Assignee: Survival Technology, Inc., Bethesda, Md.

[21] Appl. No.: 885,164

[22] Filed: Jul. 14, 1986

[51] Int. Cl.⁴ .............................................. A61M 5/24
[52] U.S. Cl. ..................................... 604/200; 604/205
[58] Field of Search ............... 604/200, 201, 202, 204, 604/205, 206, 220, 900

[56] References Cited

U.S. PATENT DOCUMENTS

| | | | |
|---|---|---|---|
| 3,424,155 | 1/1969 | Sarnoff | 604/200 |
| 3,450,135 | 6/1969 | Sarnoff | 604/200 X |
| 3,974,832 | 8/1976 | Kruck | 604/205 |
| 4,240,423 | 12/1980 | Akhavi | 604/900 X |
| 4,392,491 | 7/1983 | Takasugi et al. | 604/900 |

*Primary Examiner*—John D. Yasko
*Attorney, Agent, or Firm*—Witherspoon & Hargest

[57] ABSTRACT

A cartridge assembly having a cylindrical body, with its forward end being packed down to form an annular flange, a hub fitted on the annular flange, a diaphragm seal positioned on the forward face of the annular flange and held in sealing position by the hub fitted on the annular flange, a piston slidably carried in the rearward portion of the body, a liquid medicament held in the body in the space between the diaphragm and the piston, the hub being made of transparent plastic material and having a first cylindrical portion having an internal diameter sized to fit over the annular flange of the cartridge, a second cylindrical portion extends from the first cylindrical portion and has a diameter less than the first cylindrical portion, a third cylindrical portion extends from the second cylindrical portion and has a diameter less than the second cylindrical portion, a fourth cylindrical portion extends from the third cylindrical portion and has a diameter less than the third cylindrical portion, the fourth cylindrical portion having an internal diameter sized to receive the non-patient end of the needle, the chamber formed by the second cylindrical portion constitutes the chamber for the ballooning of the diaphragm when under medicament pressure, this chamber being provided with a spike having its point directed toward the diaphragm and adapted to pierce same upon sufficient ballooning thereof.

8 Claims, 4 Drawing Figures

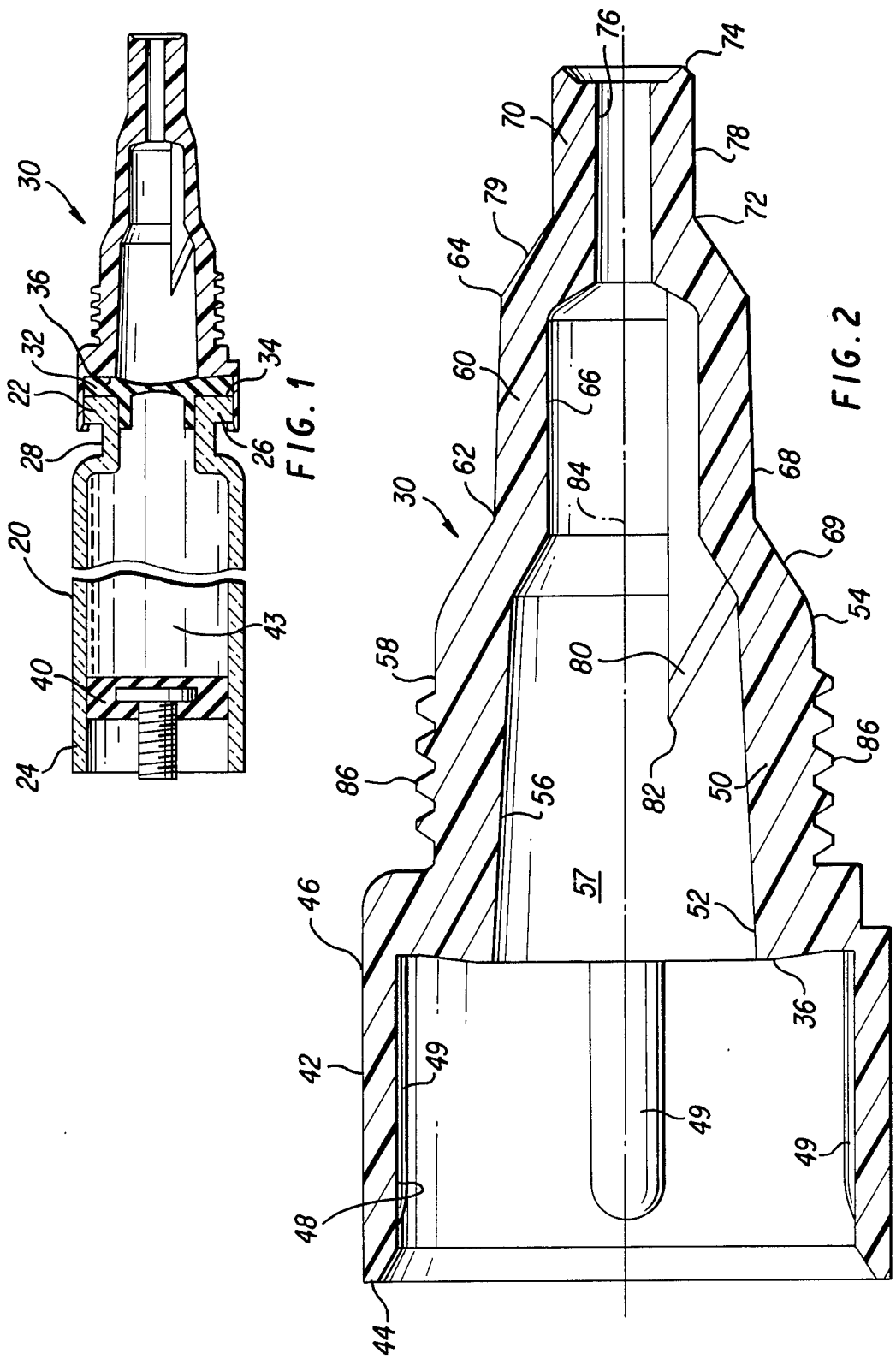

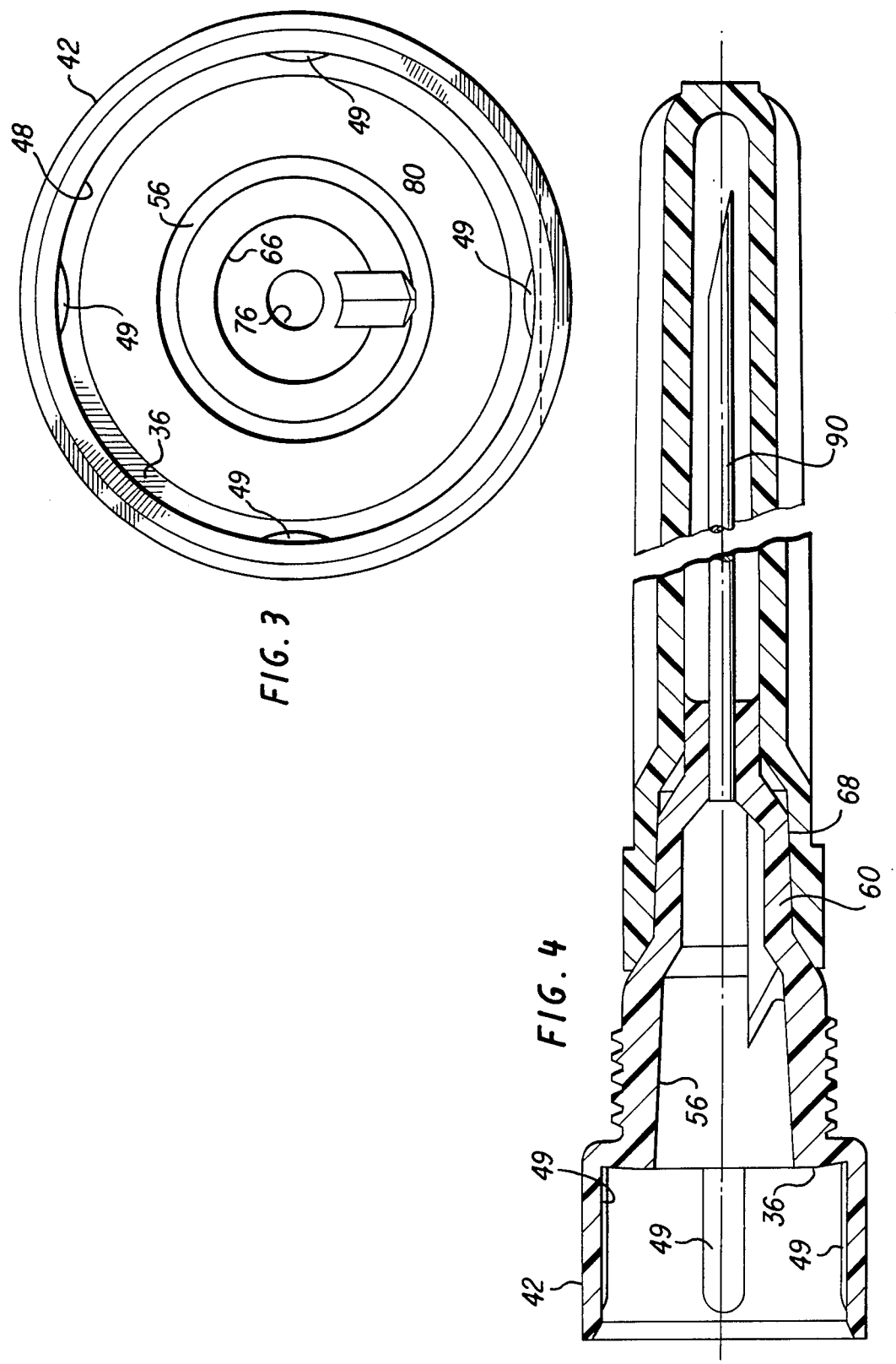

CARTRIDGE WITH UNIVERSAL PLASTIC HUB

This invention relates to syringe cartridge assemblies and more particularly a cartridge assembly which includes a clear plastic hub adapted to interface with many types of cartridge components and syringe systems.

BACKGROUND AND OBJECTS

The industry has for some time been interested in replacing the more or less conventional metal hub with a hub made of plastic material, particularly clear plastic material.

Obviously one of the first considerations is to determine what plastics would be suitable for use in hub construction. In this connection, Swenson in U.S. Pat. No. 4,581,024 states that hubs may be made of a wide variety of rigid materials such as plastics, metals, ceramics and the like. Thermoplastics are apparently a popular choice due to low cost and compatability with many liquid medicaments. In addition, a wide variety of materials may be used in making cannulas. In general, the most popular material is high grade stainless steel. A wide variety of adhesives such as hot melt adhesive, heat curable adhesive, UV curable adhesive and two-part epoxy are suitable for bonding the cannula to the hub. In most situations choices of materials are conditioned upon the types of sterilization being used.

In fact the making of cartridge hubs from plastic material is well known in the prior art. For example, Keller U.S. Pat. No. 3,372,697 discloses plastic hubs wherein the materials may be either polypropylene or polycarbonate.

For a more recent description of plastic hub development attention is directed to Akhavi U.S. Pat. No. 4,240,423 wherein there is disclosed a transparent polycarbonate hub provided with a viewing chamber just rearward of the cannula rearward end for observing whether or not a blood vessel has been punctured by observing the appearance of blood in said chamber after aspiration. Further, this patent discloses use of an expoxy adhesive for securing the needle in the hub and yet have the unit, i.e. hub and needle, autoclavable at temperatures of 240° and 260° F.

It is interesting to note that Akhavi has concerned himself with sterilization and has chosen plastics and adhesives which will withstand autoclave temperatures of 240° to 260° F.

As noted from the title of this specification, not only is a plastic hub being provided but it is capable of cooperating with many types of medicaments dispensing apparatus. This concept has found its way into the prior patented art. More specifically attention is directed to the patent to Elias U.S. Pat. No. 3,380,452 which relates to a cartridge-syringe unit comprising a unitary, generally cylindrical hollow body of plastic material. At one end the body has a reduced axially extending nose portion, the nose portion having a first region with a diameter sized to fit a cartridge holder, a second region forward of said first region and having a second predetermined diameter less than said first diameter and adapted to have affixed thereto the mounting means of a standard Luer type needle, a third region forward of said second region, said third region having a third predetermined diameter less than said second diameter and adapted to receive the end of a flexible cannula cover thereon, and a bore extending through said integral reduced nose portion axially thereof and opening at its proximal end into said hollow body and at its end out of said third region. Preferably, said first region has means thereon for fixing said unit in a cartridge holder against axial movement therein and, in a most preferred form of said means, the latter comprise a screw-thread raised on the circumferential surface of said first region.

Further, Keller U.S. Pat. No. 3,372,697 in FIG. 4 shows a hub having threads 47 adapted to threadedly cooperate with threads on the forward portion of a cartridge holder.

A large number of cartridge assemblies use a diaphragm type stopper to seal off the cannula end of the cartridge. These diaphragms are generally resilient and are ruptured by forward pressure of the medicament caused by the forward movement of the cartridge piston. In other arrangements a spike or fang may be provided in the hub adjacent the diaphragm whereby upon ballooning of the diaphragm the spike will pierce the diaphragm to allow outward flow of the medicament.

The use of fangs or spikes to burst the diaphragm in a cartridge unit is known in the prior art. Sarnoff U.S. Pat. No. 3,424,155 discloses a burstable diaphragm seal wherein the hub is provided with a plurality of spikes adapted to engage and burst the seal when it balloons forwardly under pressure from the medicament in the cartridge.

In some instanced the non-patient end of the cannula is sharpened and made to extend into the chamber where the expanding diaphragm balloons so that the sharpened end may pierce and rupture the diaphragm.

For a showing in the prior art wherein the non patient end of a needle is sharpened and projected into the chamber, and the diaphragm type stopper expands upon forward movement of the cartridge piston, attention is directed to Sie et al U.S. Pat. No. 3,695,478 entitled "Flexibly Deformable Stopper For A Hypodermic Syringe". As shown in FIG. 4, a sharp tip 75 of the non patient end of the needle 61 extends into chamber 65 which is the chamber into which the diaphragm expands prior to bursting. It is expected that the diaphragm will burst before it touches the needle end 75. However, if for any reason the diaphragm does expand to such distance without bursting the sharp end 75 will pierce the diaphragm. It is further stated that other sharp elements other than a needle end may be provided in the needle holder 63 for such purpose. Sarnoff U.S. Pat. No. 3,380,449 entitled "Cartridge With Burstable Seal" discloses a similar arrangement wherein the non patient end of a needle extends into the chamber into which the diaphragm balloons for bursting. As the final resort, over expansion without bursting will be cured by piercing of the diaphragm by the needle end.

Keeping in mind the art discussed earlier, it is an object of this invention to provide a cartridge unit having a universal transparent plastic hub capable of a multitude of functions provided by a hub having a four step, graduated construction.

It is yet another object of this invention to provide a universal hub as set forth in the previous object and wherein each step of the four step construction provides at least one specific function.

The foregoing and additional objects and advantages will become more apparent upon reference to the following drawings and detailed description covering a preferred embodiment of this invention.

IN THE DRAWINGS

FIG. 1 is a sectional view of the cartridge assembly of this invention,

FIG. 2 is a section view of the plastic hub of this invention,

FIG. 3 is a plan view of the hub looking forwardly through the largest opening therein and FIG. 4 is a sectional view showing the hub with the cannula fitted therein, and a guard fitted over the cannula onto the hub.

DETAILED DESCRIPTION

Referring to FIG. 1 of the drawings, there is shown a more or less general cartridge combination which includes a cylindrical glass body 20 having a forward end portion 22 and a rearward end portion 24. The forward end portion 22 is formed into a necked down portion comprising an annular flange 26 having an outside diameter slightly less than that of the cylindrical body 20. A circular groove 28 extends between and connects the forward portion of the body and the annular flange 26. A transparent plastic hub 30 is fitted onto the annular flange 26 with a sealing diaphragm 32 positioned on the forward face 34 of the annular flange 26 and held thereagainst by shoulder 36 of the hub 30. A piston 40 is slidably carried in the cylindrical body 20 and acts as the rearward seal for the medicament 43 carried within the body 20 between the piston 40 and the diaphragm 32.

As best illustrated in FIGS. 2 and 3 the clear plastic hub 30 comprises a first cylindrical portion 42 having a rearward end portion 44 and a forward end 46 with an internal surface 48 sized to fit over the annular flange 26 of the necked down portion of the cartridge body 20.

A second cylindrical portion 50 has a rearward end portion 52 and a forward end portion 54 with an inner surface 56 and an outer surface 58 and is connected to the first cylindrical portion 42 by means of shoulder portion 36 generally slightly angled outward to insure no slipage or movement of the sealing diaphragm 32 after final assembly.

A third cylindrical portion 60 is positioned forwardly of the second cylindrical portion 50 and is coaxial therewith. Said third cylindrical portion has a rearward end portion 62 and a forward end portion 64 with an inner surface 66 and an outer surface 68. The outer diameter of the third cylindrical portion 60 is less than that of the second cylindrical portion 50 whereby the forward end 54 of the second cylindrical portion 50 is connected to the rearward end 62 of the third cylindrical portion 60 by means of sloping portion 69.

A fourth cylindrical portion 70 is positioned forwardly of the third cylindrical portion 60 and is coaxial therewith. Said fourth cylindrical portion 70 has a rearward end 72 and a forward end 74 with an inner surface 76 and an outer surface 78. The outer diameter of the fourth cylindrical portion 70 is less than that of the third cylindrical portion with the forward end 64 of the third cylindrical portion 60 being connected to the rearward end 72 of the fourth cylindrical portion 70 by a connecting portion 79 sloping inwardly and forwardly. The longitudinal hole formed by inner surface 76 is diametered such that one diameter will accommodate a range of gauges of needles assembled in the hub 30.

The outer surface 68 of the third cylindrical hub portion 60 has a 6° taper extending inwardly and forwardly to accommodate needle or other mounting means provided with the standard Luer taper. The inner surface 56 of the second cylindrical portion 50 forms a diaphragm expansion chamber 57 provided with an integral spike 80 having a pointed tip 82 directed rearwardly and offset from the central axis 84 of the hub.

The outer surface 58 of the second cylindrical portion 50 is provided with peripheral threads 86 extending from adjacent shoulder 36 to near the forward end 54 of said second cylindrical portion 50. Said threads 86 are sized to cooperate with like means on cartridge holders or the like as illustrated in Keller U.S. Pat. No. 3,372,697. The inner surface 48 of the first cylindrical portion 42 is provided with four longitudinally extending ribs 49 which serve to frictionally engage the annular flange 22 to retain the hub assembly on the annular flange 22 for assembly purposes. After the hub is so positioned on the annular flange the rearward end portion 44 of the first cylindrical portion is rolled down over the round edge of said annular flange as shown in FIG. 1.

FIG. 4 shows the cannula assembly ready for assembly onto the annular flange 22 of the cartridge body 20. More particularly, needle 90 is fitted into the hole formed by wall 76 in the fourth cylindrical portion 70. The needle 90 is sealed in place by a UV curable urethane adhesive. A needle shield 92 is fitted over the exposed needle portion and frictionally held on sloping surface 68 of the third cylindrical portion 60.

The hub is made by the injection molding process and of a radiateable polycarbonate which is substantially clear. In view of the injection molding many cleaning operations used for metal hubs are eliminated which is of course advantageous.

The hub/needle guard interface, which is a critical issue when metal hubs are used, is no longer a great concern with the plastic to plastic engagement. Such interface are quite predictable and reliable and therefore quality control is made much easier than heretofore.

As briefly mentioned earlier, the assembly of the hub to the glass annular flange of the cartridge body is done using rapidly rotating wheels. The force and friction developed thereby cause the end portion of the plastic hub to fit down over the annular flange 22 as shown in FIG. 1.

The presently used diaphragm, which isolates the drug or product from the hub area, must be ruptured to be used. This rupture must be of such kind as to allow the full passage of the product both for aspiration and extrusion. Currently, the present metal hub system uses a "butt end" needle point on the non-patient end of the needle. This needle point is positioned at a particular place within the hub dome to attain the best kind of rupture by coming into contact with the expanding diaphragm at the point where the elastomer approaches the crystalline state. In contrast, the present hub has a built-in spike integral therewith. This feature eliminates the need and expense of grinding both ends of the cannula and being sure that it is positioned correctly in assembling same.

A brief description of the assembly of the cartridge unit of this invention is as follows:

1. The hub is injection molded using a polycarbonate.
2. The hub is plasma treated for cleanliness and to ensure that the quality of the adhering surfaces of the hub are as required.
3. The needle is placed in the hub and a small measure of UV curable adhesive material is dispensed into the hub-needle interface, which "wicks" itself down the needle, ensuring that the maximum adhering surface is attained.

4. The adhesive is then cured under a UV radiant-producing fixture which "fixes" the needle into the hub.
5. The needle guard is then put on and the assemblies are then bagged according to the system of sterilization.
6. The needle, hub, and guard assemblies are sent through a radiation sterilizer, or through a steam autoclave.
7. Once in the clean room, the needle, hub, and guard assemblies are put into a machine which introduces the diaphragm into place inside the needle, hub, and guard assembly, making it a needle, hub, guard and diaphragm assembly.
8. The needle, hub, guard and diaphragm assemblies are then fed through the filling and assembly machinery where they are secured to the tooled ends of glass cartridges.

A brief summary of this invention and its use as well as its relation to other systems follows.

The apparatus of this invention interfaces with most syringe systems. The stand-alone filled cartridge can be secured in a number of holders, or can be used with a snap-on system of fingergrips, or in its own disposable holder. It can also interface with the SoluJect System, which is a disposable system for reconstituting two different drugs.

Once the cartridge assembly is placed in a holder and a plunger rod has been screwed onto the metal insert of the plunger, the user then exerts force on the plunger rod, creating pressure that expands the rubber diaphragm until the elastomer fills the inside of the diaphragm chamber and comes into contact with the molded-in spike. This causes the diaphragm to rupture.

Once the diaphragm is ruptured, the needle guard is removed and the syringe is ready for injection.

In the case of IM injection, the syringe is aspirated to be sure that blood is not present. With other syringes and syringe systems, the unit must be aspirated until evidence of blood appears in the cartridge, mixed with the drug. With the present system, blood would immediately be seen in the diaphragm chamber, magnified by the fresnel effect of the molded-in threads around the outside surface of said chamber. Conversely, in IV injection, the user MUST see the presence of blood in the syringe to confirm proper subsequent drug administration.

It is thus apparent that the cartridge assembly using the universal hub of this invention can serve the combined functions formerly requiring a plurality of cartridge assemblies with many different types of holders.

What is claimed is:

1. In a cartridge assembly comprising a cylindrical body, said body having a forward end and a rearward end, the forward end being necked down to form an annular flange, a hub fitted on the annular flange, a diaphragm seal positioned on the forward face of the annular flange and held in sealing position by the hub fitted on the annular flange, a piston slidably carried in the rearward portion of the body, a liquid medicament held in the body in the space between the diaphragm and the piston, said hub being made of transparent plastic material and comprising:

(1) a first cylindrical portion having a rearward end and a forward end and an inner and an outer surface, the internal diameter of the first cylindrical portion being sized to fit over the annular flange of the necked down portion of the cartridge body, (2) a second cylindrical portion having a rearward end and a forward end and an inner and an outer surface, said rearward end extending forwardly from the forward end of the first cylindrical portion and coaxial with said first cylindrical portion, the second cylindrical portion having a diameter less than that of the first cylindrical portion, a shoulder portion generally perpendicular to the axis of the two cylindrical portions and connecting the rearward end of the second cylindrical portion to the forward end of the first cylindrical portion;

(3) a third cylindrical portion having a rearward end and a forward end and an inner and an outer surface, said rearward end extending forwardly from the forward end of the second cylindrical portion and coaxial with the second cylindrical portion, the third cylindrical portion having a diameter less than that of the second cylindrical portion and having its rearward end connected to the forward end of the second cylindrical portion, (4) a fourth cylindrical portion having a rearward end and a forward end and an inner and an outer surface, said rearward end connected to the forward end of the third cylindrical portion and coaxial with the third cylindrical portion, the fourth cylindrical portion having a diameter less than that of the third cylindrical portion, (5) the internal diameter of the axial hole in the fourth cylindrical portion being sized to receive the non patient end portion of a needle, (6) the outer surface of the third cylindrical portion being tapered 6° inwardly and forwardly so as to accommodate mounting means embodying the standard Luer taper, (7) the diaphragm chamber defined by the inner surface of the second cylindrical portion being provided with a spike, said spike having a pointed portion directed toward the rearward end of the second cylindrical portion and offset from the axis of said second cylindrical portion, the point of said spike being spaced from the rearward end of the second cylindrical portion a sufficient amount so that the diaphragm will normally balloon and then burst in the diaphragm chamber upon contacting the spike, (8) the outer surface of the second cylindrical portion being provided with peripheral threads extending from adjacent the shoulder portion connecting the first and second cylindrical portions to near the forward end of the second cylindrical portion, said threads being sized to cooperate with like means on a cartridge holder, and the threads acting as magnifying means to aid in viewing within the diaphragm chamber whereby it will be easy to look through the threads and in a magnified rendition see whether or not blood appears in said chamber to thereby indicate that a blood vessel has been pierced by the needle in the injection procedure.

2. In a cartridge assembly comprising a cylindrical body, said body having a forward end and a rearward end, the forward end being necked down to form an annular flange having an outside diameter slightly less than that of the cylindrical body, a circular groove extending between the forward end of the body and the annular flange, a hub fitted on the annular flange, a diaphragm seal positioned on the forward face of the annular flange and held in sealing position by the hub fitted on the annular flange, a piston slidably carried in the rearward portion of the body, a liquid medicament held in the body between the diaphragm and the piston, said hub being made of transparent plastic material and comprising:

(1) a first cylindrical portion having a rearward end and a forward end and an inner and an outer surface, the internal diameter of the first cylindrical portion being sized to fit over the annular flange of the necked down portion of the cartridge body, (2) a second cylindrical portion having a rearward end and a forward end and an inner and an outer surface, said rearward end extending forwardly from the forward end of the first cylindrical portion and coaxial with said first cylindrical portion, the second cylindrical portion having a diameter less than that of the first cylindrical portion, a shoulder portion generally perpendicular to the axis of the two cylindrical portions and connecting the rearward end of the second cylindrical portion to the forward end of the first cylindrical portion, (3) a third cylindrical portion having a rearward end and a forward end and an inner and an outer surface, said rearward end extending forwardly from the forward end of the second cylindrical portion and coaxial with the second cylindrical portion, the third cylindrical portion having a diameter less than that of the second cylindrical portion, a sloping portion connecting the rearward end of the third cylindrical portion to the forward end of the second cylindrical portion, (4) a fourth cylindrical portion having a rearward end and a forward end and an inner and an outer surface, said rearward end extending forwardly from the forward end of the third cylindrical portion and coaxial with the third cylindrical portion, the fourth cylindrical portion having a diameter less than that of the third cylindrical portion, a connecting portion sloping inwardly and forwardly toward the axis of the fourth cylindrical portion and connecting the rearward end of the fourth cylindrical portion to the forward of the third cylindrical portion, (5) the internal diameter of the axial hole in the fourth cylindrical portion being sized to receive the non patient end portion of a needle, (6) the outer surface of the third cylindrical portion being tapered 6° inwardly and forwardly so as to accommodate mounting means embodying the standard Luer taper, (7) the diaphragm chamber defined by the inner surface of the second cylindrical portion being provided with a spike, said spike having a pointed portion directed toward the rearward end of the second cylindrical portion and offset from the axis of said second cylindrical portion, the point of said spike being spaced from the rearward end of the second cylindrical portion a sufficient amount so that the diaphragm will normally balloon and then burst in the diaphragm chamber upon contacting the spike, (8) the outer surface of the second cylindrical portion being provided with peripheral threads extending from adjacent the shoulder portion connecting the first and second cylindrical portions to near the forward end of the second cylindrical portion, said threads being sized to cooperate with like means on a cartridge holder, and the threads acting to magnify matter within the diaphragm chamber whereby it will be easy to look through the threads and in a magnified rendition see whether or not blood appears in said chamber to thereby indicate that a blood vessel has been pierced by the needle in the injection procedure.

3. The invention as set forth in claim 2 and wherein the transparent plastic material is a polycarbonate.

4. The invention as set forth in claim 3 and wherein the hub is provided with a needle fitting into the axial hole in the fourth cylindrical portion of the hub.

5. The invention as set forth in claim 4 and wherein the needle is secured in the axial hole by a UV curable urethane.

6. The invention as set forth in claim 5 and wherein the polycarbonate hub and the UV cured urethane adhesive holding the needle in the hub will both tolerate sterilization either by a steam autoclave or a radiation sterilizer.

7. The invention as set forth in claim 2 and wherein the hub is retained on the annular flange of the cartridge body by rolling the back end portion of the first cylindrical portion down over said flange.

8. The invention as set forth in claim 2 and wherein the inside surface of the first cylindrical portion of the hub is provided with a plurality of beadings extending parallel to each other and fore and aft on said surface.

* * * * *